United States Patent [19]

Daou et al.

[11] Patent Number: Plant 7,491

[45] Date of Patent: Apr. 9, 1991

[54] ARTHUR CHERIMOYA TREE

[76] Inventors: Arthur J. Daou, A. Daou Bldg., Edde Road, Byblos, Jbail, Lebanon; Suzanna Daou, 5 Marine Ave., Westport, Conn. 06880

[21] Appl. No.: 385,561

[22] Filed: Jul. 27, 1989

[51] Int. Cl.[5] ..... A01H 5/00

[52] U.S. Cl. ..... Plt./33

[58] Field of Search ..... Plt./33

[56] References Cited

U.S. PATENT DOCUMENTS

P.P. 656 3/1945 Ott ..... Plt. 33

*Primary Examiner*—James R. Feyrer

[57] ABSTRACT

A new *Annona cherimoya* tree named Arthur, characterized by the tree's relative hardiness and resistance to cold and to the Mediterranean fruit fly, and the fruit's superlative flavor and extremely small number of seeds.

3 Drawing Sheets

BACKGROUND OF THE INVENTION

A new and distinct variety of the cherimoya tree, botanically known as *Annona cherimoya,* and referred to by the variety name Arthur.

SUMMARY OF THE INVENTION

Arthur was discovered by us as a mutation of a wild variety of cherimoya grown from seed in our orchard in the coastal town of Byblos in the country of Lebanon. The characteristics hereinafter described are such as have been observed in trees grown in that geographical region, i.e. West-coast Mediterranean littoral.

When the new seedling had grown long enough to show indications of promise (i.e. once it had borne fruit), it was asexually reproduced by means of budwood grafted onto unnamed local (Lebanese) varieties of *Annona cherimoya* and *Annona muricata* understocks. The asexually reproduced trees set fruit which matured in the third year after grafting. The characteristics of the new variety are reproduced in stock similarly grafted.

The characteristics are not reproduced when propagated from seed, but there are numerous similarities, and we have discovered a few distinct sub-varieties over the past 12 years that are similar but inferior overall to Arthur. One outstanding common characteristic of trees grown from Arthur seed is that they provide rootstock superior in hardiness and cold-resistance to most available varieties.

BOTANICAL DESCRIPTION

Production Characteristics

Figure 1:
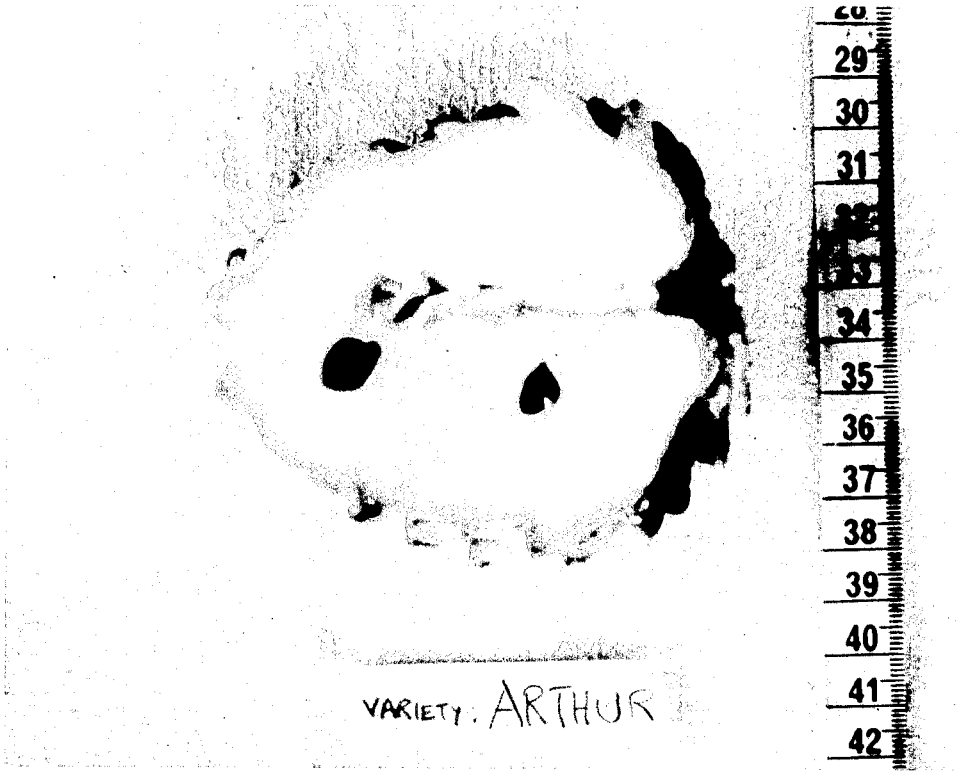
FIG. 1 depicts a typical specimen of the fruit of the variety in cross section showing flesh and seed placement and coloration.
Figure 2:
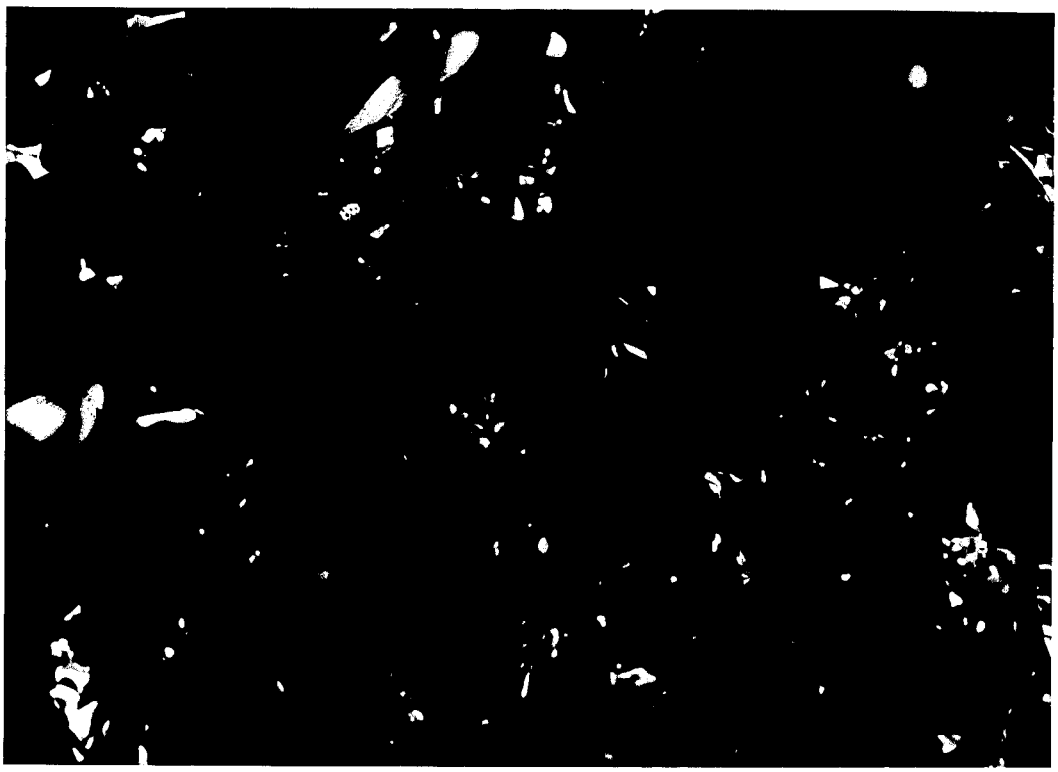
FIG. 2 shows, at an angle from below, the branching, bark, fruit load and foliage of the tree in late fruit forming stage.
Figure 3:
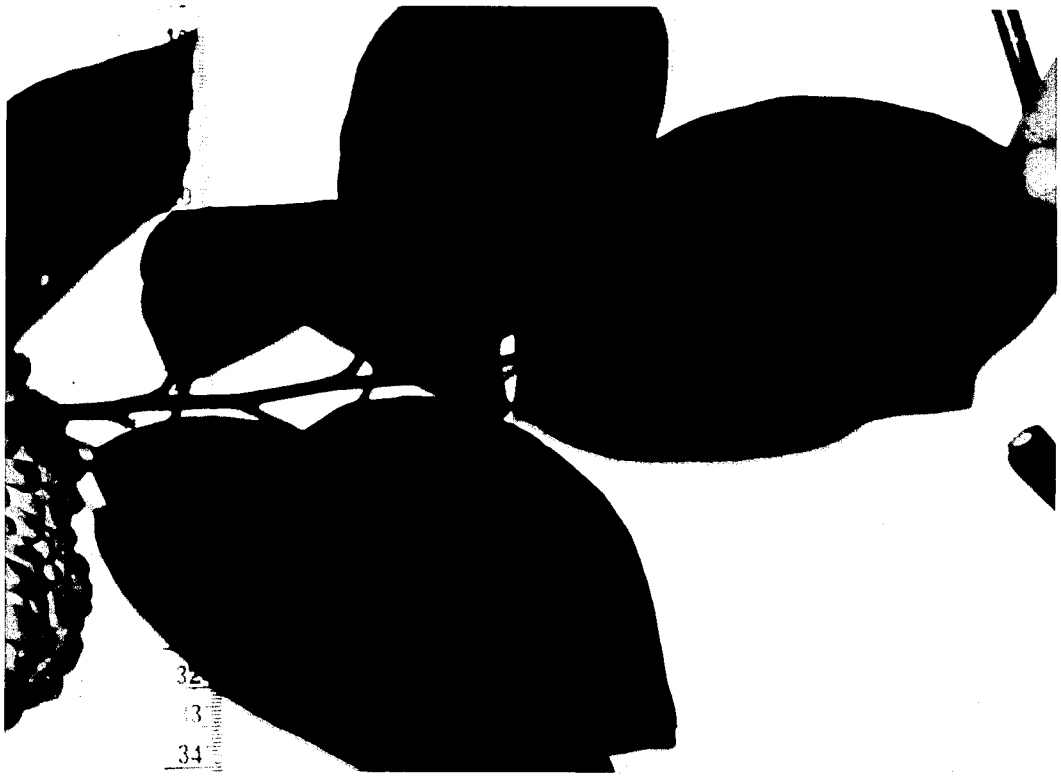
FIG. 3 shows the terminal portion of a fruit bearing stem and details the leaf venation, margin and color of leaves and current season bark.
Figure 4:
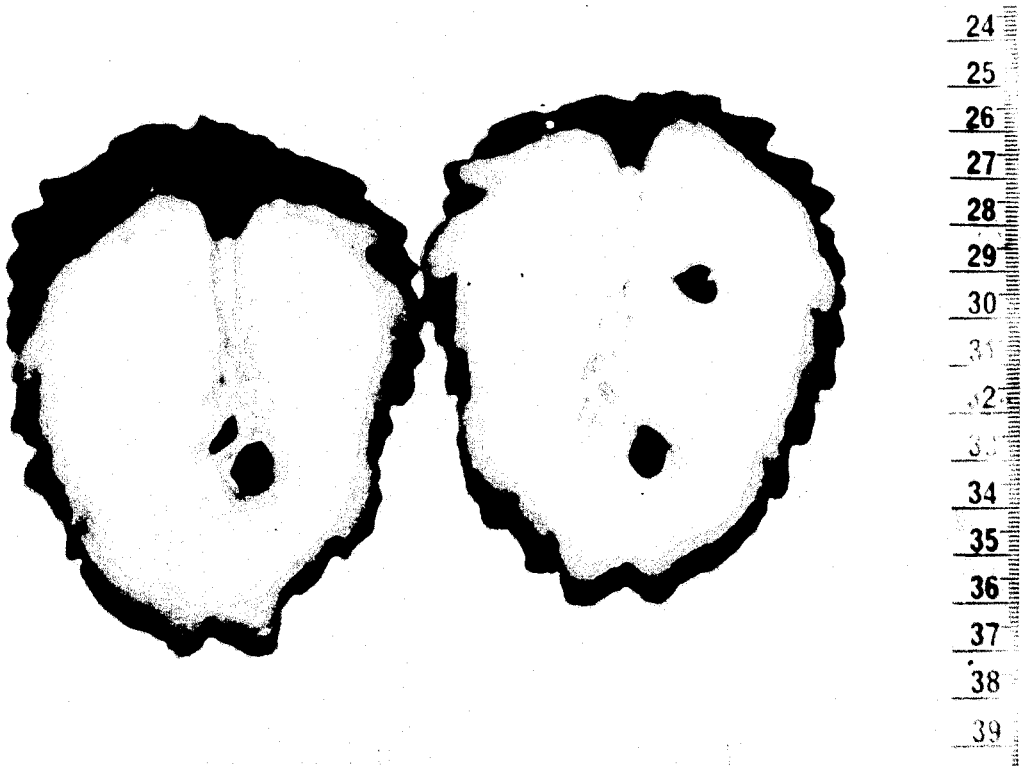
FIG. 4 depicts a mature fruit sliced in half along the axis to reveal seeds and their placement, the stem basin, and the flesh; and, FIG. 5 is a side view of a mature fruit showing stem, a leaf, and the surface coloration of the surface protuberances and recesses of the fruit surface.
Figure 5:
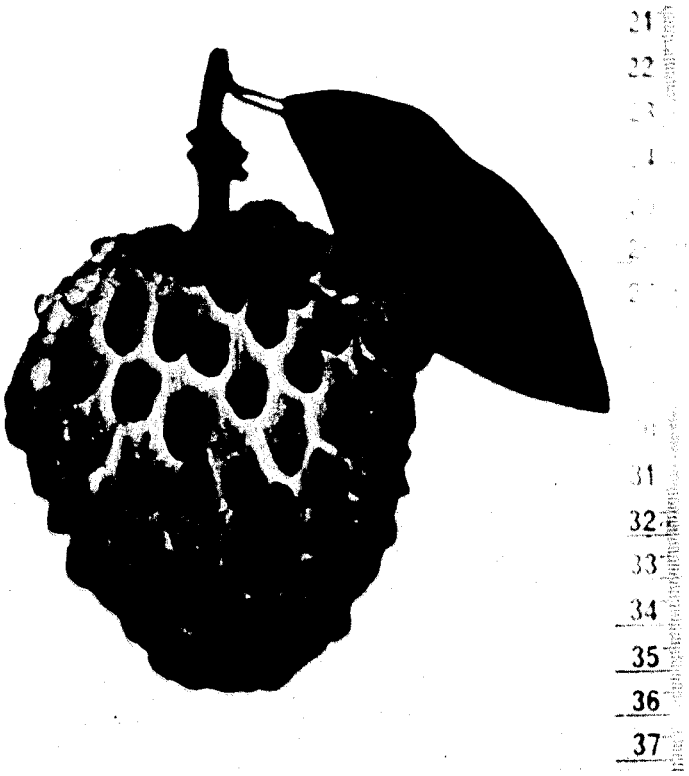

This new variety is a bearer of moderate crops, and of very heavy crop when hand-pollinated. A 10 year-old tree will bear 40 kg (90 lbs) of fruit; to about 80 kg (180 lbs.) with regular hand-pollination. At 15 years, the tree will bear 75 kg (165 lbs); to 125 kg (275 lbs); and at 20 years, 100 kg (220 lbs); to 250 kg (550 lbs).

It has indicated frost resistance at sustained temperatures of −2 to 0 degrees Celsius (28.4 to 32 degrees Fahrenheit) for over 48 hours and is less sensitive than most varieties to sustained cold and excessive rainfall (i.e. tree is undamaged, fruit does not readily blacken or split as most varieties do).

Arthur fruits have not been attacked by Mediterranean fruit flies, although other cherimoya varieties and other fruit trees in close proximity have been severely affected.

Fruit

Fruit of this new variety ranges from medium to very large, with diameters from 7.5 cm. to 18 cm. (3" to 8.5"); and lengths from 9 cm. to 18 cm. (3.5" to 7"). Fruit weight varies from 200 grams to 800 grams (7 oz. to 28 oz.); to over 1.5 kg. (53 oz.) in exceptional specimens (approx. 1 in every 100 fruits). Fruit size has a much wider variance without hand-pollination, but Arthur fruits generally average 300 to 500 grams (10.5 oz. to 17.5 oz.) in weight.

The fruit is relatively uniform in shape regardless of size, and resembles a large pine cone, with "bumps" or protuberances measuring 0.5 to 1.5 cm. in length (1/5" to 3/5"). A distinctive characteristic is the one overgrown "bump" that protrudes up to 2.5 cm. (1") more than the rest, giving this variety an unmistakeable appearance. Stems vary from 2.5 to 7.5 cm. (1" to 3") in length and are of medium caliper. Fruit holds well on the stem and is not subject to drop unless allowed to ripen on the tree.

The skin of the fruit is covered with protuberances (or "bumps" as described above), and is smooth and moderately thin between the bumps. The larger the fruit, the more space between the "bumps", and in smaller fruits the "bumps" are contiguous at their bases. The skin has a matte appearance and ranges from light yellow-green to a pine green in color (usually Pantone® Green 5825U, with Pantone® Yellow 393U in the spaces between).

The flesh of the fruit is uniformly ivory- or cream-white. The texture of the flesh is smooth and creamy, without discernible fiber. It softens uniformly when mature, and the flesh is edible all the way to the outer skin. Fruits will ripen fully if left on the tree, and this often happens to "mature" fruits overnight or in 2 to 3 days after heavy rainfall followed by warm weather. Mature fruits ripen faster if left on the tree in the Fall than in the Winter; and fruit lasts much longer on the tree in colder weather. At such times a "ready-to-pick" fruit can last 8 weeks or more on the tree without ripening.

Fruit picked "hard" tends to have superior flavor than tree-ripened fruit. The flavor overall is superb, and far surpasses any other variety currently propagated commercially in the United States, Spain, or Israel, at least as available in fruit markets in the United States, Europe or the Middle East. The flavor is at its best during the peak of the bearing season (November through January in Lebanon), and flavor declines as the season progresses (largely due to increased water content following the heavy rainfall of the Mediterranean winter).

"Mature" or "ready-to-pick" fruit are fruits that when picked will ripen fully and uniformly.

The skin of the fruit is medium thin and smooth, and there is very little tendency to crack.

Flowers begin to appear in mid-May, and the tree continues flowering until mid-September. The flower buds are medium to quite large (and begome larger as the season progresses), conic in shape and tapering to the bottom. Fruits begin to set in early July, and continues through the end of August. Hand-pollination becomes more effective as the summer progresses. The success rate of hand-pollination in early (Summer) flowers is only about 20% to 25%. It rises to about 75% in August and September.

The fruiting season generally extends from mid-October to late February, although late-set fruit will hold on the tree until the end of April, and even occasionally into June.

Fruits ripen 5 to 10 days from date picked, at room temperature, and will keep 2 to 5 days more if refrigerated in a home refrigerator. Limited experimentation shows that if the fruit is refrigerated at 8 to 10 degrees Celsius continuously, storage life is 12 to 18 days prior to ripening. Slight blackening of the "bumps", especially at their tips may occur due to over-ripeness or bruising from excessive handling. However, in common with other varieties, the Arthur cherimoya does not respond well to refrigeration.

A very distinctive and important characteristic is the very small number of seeds, approximately 5–15 seeds per average fruit.

Tree

The Arthur tree is medium to large-sized, growing to over 10 meters (approx. 30 to 35 feet) in height.

The Arthur tree is relatively hardy and is not as sensitive to extremes of either hot (it has survived undamaged through 7 days of a heat wave averaging 43 degrees Celsius at mid-day); or cold weather (−2 degrees Celsius for 2 full days); or strong winds compared to other commercially-fruiting varieties, which sustained very heavy damage under the same conditions.

The original Arthur tree is now 24 years old and is approximately 9 meters (30 feet) tall, spreading evenly to about 14 meters (46 feet) in diameter at its widest. The growth is vigorous and spreading, with moderately dense foliage. It has a medium thick trunk about 1.6 meters (63 inches) in diameter at 1.5 meters (5 feet) from the ground. The bark is smooth and the branches medium slender. The main trunk of a mature tree branches out at about 1.5 to 2 meters (5 to 6.6 feet) above ground level.

The overall appearance of the bark is clean and smooth, and not distinctly different from that of many cherimoya varieties. Color ranges from Pantone® Green 449C to 450C for the new growth, and Pantone® Brown 499C in the mature terminal branches.

Foliage

Leaves range from medium to large in size, being from 5 cm to 15 cm (2" to 6") in width and 10 cm to 25 cm (4" to 10") in length. They are ovate in form, with acute tip, varying to somewhat elliptic, and of medium thickness.

The color of leaves on the upper side ranges from Pantone® Green 350C to 357C, while the underside is lighter and duller in color. Leaf coloration varies with changes in season and differences in soil content. Iron (Fe) deficiency in the soil can cause extreme yellowing of the leaves.

Like other cherimoyas, Arthur is deciduous. However, it sheds its leaves around the middle of April, which is about 6 weeks later than many other commercial varieties. By the end of May the tree is almost completely bare of old growth. New leaf growth begins at the end of April, and will continue through the end of October.

The veining of the leaves is somewhat pronounced, and lighter in color than the leaf. The leaf margins are very regular in form.

We claim:

1. The new variety of *Annona cherimoya* substantially as shown and described herein, being distinguished for its ability to produce fruit of exceptional flavor with an unusually small number of seeds. The tree of this variety also being notable for its relative hardiness and resistance to extremes of heat and cold, and not susceptible to the Mediterranean Fruit Fly.

* * * * *